(12) United States Patent
Arnaud (10) Patent No.: US 7,250,159 B1
(45) Date of Patent: Jul. 31, 2007

(54) COMPOSITIONS COMPRISING AT LEAST ONE ESTER OF AT LEAST ONE HYDROXYLATED ALIPHATIC COMPOUND

(75) Inventor: Pascal Arnaud, L'Hay les Roses (FR)

(73) Assignee: L'Oréal S.A., Paris (FR)

( * ) Notice: Subject to any disclaimer, the term of this patent is extended or adjusted under 35 U.S.C. 154(b) by 81 days.

(21) Appl. No.: 09/705,833

(22) Filed: Nov. 6, 2000

(30) Foreign Application Priority Data

Nov. 4, 1999 (FR) .................................. 99 13812

(51) Int. Cl.
*A61Q 1/04* (2006.01)
*A61Q 1/06* (2006.01)

(52) U.S. Cl. .......................................... 424/64; 424/63

(58) Field of Classification Search ................ 424/401, 424/64, 70.7, 70.1
See application file for complete search history.

(56) References Cited

U.S. PATENT DOCUMENTS

| 5,468,897 A | 11/1995 | Shroot et al. .................. 560/18 |
| 5,932,197 A * | 8/1999 | Arnaud ......................... 424/64 |
| 5,959,130 A * | 9/1999 | Walele et al. ............... 554/220 |

FOREIGN PATENT DOCUMENTS

| FR | 2 649 977 | 1/1991 |
| FR | 2 745 580 | 9/1997 |
| GB | 590 386 | 7/1947 |

OTHER PUBLICATIONS

Finetex Inc., "Finsolv BCO-115 (castor oil benzoate)", Finetex Homepage: Product Index—Technical Data Sheet, 1999, XP002144802.

* cited by examiner

*Primary Examiner*—Jyothsna Venkat
(74) *Attorney, Agent, or Firm*—Finnegan, Henderson, Farabow, Garrett & Dunner, L.L.P.

(57) ABSTRACT

Compositions comprising at least one ester which comprises at least one aromatic group, which is liquid at room temperature and which is derived from esterification with (i) at least one aromatic acid of (ii) at least one hydroxyl group of at least one hydroxylated aliphatic compound chosen from hydroxylated aliphatic acids and esters of hydroxylated aliphatic acids, wherein said at least one hydroxyl group is chosen from pendant hydroxyl groups and terminal hydroxyl groups. The inventive compositions may be used for, for example, making up the face, body or superficial body growths of human beings and may constitute, for example, a lipstick, a lip gloss, a tattooing product, an eye shadow, a mascara, a product for caring for the hair or a nail varnish.

29 Claims, 1 Drawing Sheet

Figure 1.

COMPOSITIONS COMPRISING AT LEAST ONE ESTER OF AT LEAST ONE HYDROXYLATED ALIPHATIC COMPOUND

The present invention is directed to a composition for making up and for care of at least one keratinous material comprising at least one ester having high molecular mass which may confer at least one notable cosmetic property on the composition, such as gloss, slip, coverage and hold over time. The at least one keratinous material can be chosen, for example, from at least one human keratinous material, such as skin (including the scalp and both facial skin and skin on the body), lips, hair, eyelashes, eyebrows and nails.

For example, the inventive compositions may constitute a product for making up at least one keratinous material. This product may be used for the care of and/or treatment of the at least one keratinous material. According to the present invention, products for making up at least one keratinous material may be in the form of lipstick products, lip gloss products, eyeshadow products, tattooing products, mascara products, eyeliner products, nail varnish products, products for artificial tanning of skin, creams for the care of at least one keratinous material which may optionally be dyed, creams for the protection of least one keratinous material which may optionally be dyed, products for coloring hair or products for caring for hair.

Numerous cosmetic compositions deposit a film on the keratinous material on which they are applied. The gloss property of such a film is generally very important in products such as, for example, lipstick products, nail varnish products and some hair products.

It is known to those of skill in the cosmetic art that this gloss property may be obtained when the compositions comprise at least one oil having a high viscosity, a high refractive index and which is able to disperse pigments and/or fillers, if present, in a satisfactory manner. As used herein, "oil" refers to a nonaqueous medium which is liquid at room temperature (25° C.) and atmospheric pressure (760 mmHg) and which is immiscible with water in any proportion.

Traditionally, oils used to provide gloss in cosmetic compositions included:

oily polymers, such as polybutenes. Non-limiting examples of such oily polymers include those sold under the reference Indopol H100, H300 and H1500 by Amoco, which have a very high viscosity (such as greater than 28,194 cP (2819 Pa.s) at 20° C., measured with a Brookfield "DV-II+" viscometer of LV type equipped with a No. 2 rotor rotating at 0.5 tr/min) and a high refractive index (such as greater than 1.49 at 20° C.). However, these oily polymers may be very sticky and may not disperse pigments in a satisfactory manner. These disadvantages may restrict the use of these oily polymers and may limit the concentration of these oily polymers in cosmetic products; and oils of plant origin, such as castor oil which is frequently used in lipstick products. Castor oil generally has a medium viscosity (of the order of 786 cP (78.6 Pa.s) at 20° C., measured with the aforementioned viscometer rotating at 4 tr/min), a refractive index of the order of 1.475 at 25° C. and good properties of dispersing pigments. However, castor oil may absorb water, resulting in problems of stability of products in stick form, such as lipstick sticks. This is known as exudation and may result in formation of droplets of oil at the surface of the product. Exudation may be especially problematic in countries and geographical areas where there is a degree of humidity. Further, castor oil may be difficult to formulate in care products due to its sensitivity to heat and ultraviolet radiation. Specifically, this sensitivity may result in the partial decomposition of the castor oil which results in the release of an unpleasant smell. This smell is difficult to conceal even with a highly odiferous fragrance. Therefore, the use of castor oil in certain cosmetic compositions may be restricted, such as in care creams and liquid foundation products which are generally emulsions.

Castor oil comprises ricinoleic acid, which has the formula $CH_3(CH_2)_5CH(OH)CH_2CH=CH(CH_2)_7COOH$. One possibility for limiting exudation would comprise removing a hydroxyl group, specifically the acidic alcohol functional group, present on ricinoleic acid, such as, for example, converting the acidic alcohol functional group into an ester. For example, the triacetylated derivative of ricinoleic acid is known, according to The Cosmetic Toiletry and Fragrance Association, as glyceryl triacetyl ricinoleate. However, the physicochemical properties of glyceryl triacetyl ricinoleate may be less favorable than those of castor oil with respect to gloss, such as in terms of viscosity, which is generally only of the order of 230 cP at 25° C.

One subject of the present invention is compositions for caring for or for making at least one keratinous material which may overcome at least one of the aforementioned disadvantages. The inventors have discovered, surprisingly, that compositions comprising at least one ester derived from esterification, which may be complete or partial, of at least one hydroxylated aliphatic compound with at least one aromatic acid may make it is possible to obtain glossy cosmetic compositions which are homogenous as the result of good dispersion of any pigments and/or fillers present in the composition, and which do not exude when in a stick form. The inventive compositions may exhibit good spreading and slip properties and may confer at least one desirable property on a deposited film of the composition such as gloss, good hold over time (such as, for example, no change in color for at least 3 hours and/or disappearance of the make up in a homogeneous fashion), lack of unsuitable stickiness and lack of unsuitable greasiness. Further, the inventive compositions may be stable over time, such as stability for several months at room temperature (such as stability at 25° C. for over than one year), may be stable towards heat (such as stability at 47° C. for 2 months) and may be stable towards ultraviolet radiation. Finally, the inventive compositions may not emit any unpleasant smells.

Specifically, one embodiment of the present invention is directed to a cosmetic composition comprising (1) at least one particulate filler, (2) at least one wax and (3) at least one ester which comprises at least one aromatic group, which is liquid at room temperature and which is derived from esterification with (i) at least one aromatic acid of (ii) at least one hydroxyl group of at least one hydroxylated aliphatic compound chosen from hydroxylated aliphatic acids and esters of hydroxylated aliphatic acids, wherein said at least one hydroxyl group is chosen from pendant hydroxyl groups and terminal hydroxyl groups. As used herein, "hydroxyl group" refers to a substituent group of formula —OH. As used herein, "terminal hydroxyl groups" refers to hydroxyl groups at the end of a chain of a hydroxylated aliphatic compound.

Another subject of the present invention is a cosmetic composition for caring for and making up at least keratinous material comprising at least one entity chosen from emulsifying agents and waxes and at least one ester comprising at least one aromatic group which is liquid at room temperature and which is derived from esterification by (i) at least one aromatic acid of (ii) least one hydroxyl group of at least one hydroxylated aliphatic compound chosen from hydroxylated aliphatic acids and esters of said hydroxylated aliphatic acids, wherein said at least one hydroxyl group is chosen from pendant hydroxyl groups and terminal hydroxyl groups.

As used herein, "hydroxylated aliphatic compound" refers to a compound chosen from aliphatic hydroxycarboxylic acids and esters of aliphatic hydroxycarboxylic acids. According to the present invention, the non-esterified hydroxylated aliphatic acids can comprise from 2 to 40 carbon atoms (such as from 10 to 34 carbon atoms, and further such as from 12 to 28 carbon atoms) and from 1 to 20 hydroxyl groups which are capable of being esterified by at least one aromatic acid (such as from 1 to 10 hydroxyl groups, and further such as from 1 to 6 hydroxyl groups). Further, the esters of aliphatic hydroxycarboxylic acid can be derived from esterification of the carboxylic acid (—COOH) functional group of at least one aliphatic hydroxycarboxylic acid by at least one aliphatic alcohol. The aliphatic alcohol can comprise from 1 to 40 carbon atoms, such as from 3 to 30 carbons atoms, and can be chosen from aliphatic monoalcohols and aliphatic polyols. The esters of aliphatic hydroxycarboxylic acids derived from reaction of at least one aliphatic hydroxycarboxylic acid with at least one polyol can be partially or totally esterified esters.

In one embodiment, the at least one aliphatic hydroxycarboxylic compound is chosen from esters of aliphatic hydroxycarboxylic acids derived from at least one aliphatic hydroxycarboxylic acid. Thus, the at least one ester comprises at least one ester of an ester wherein the ester groups may be identical or different. In another embodiment, the at least one ester is chosen from fatty acid esters comprising at least one ester of an ester wherein the ester groups may be identical or different and wherein the fatty acid residue comprises at least 12 carbon atoms. In yet another embodiment, the at least one hydroxyl group which is esterified by the at least one aromatic acid is chosen from the terminal acidic hydroxyl groups of at least one hydroxylated aliphatic compound.

Of course, according to the present invention, the inventive composition can comprise at least two aromatic esters which are liquid at room temperature (25° C.) and atmospheric pressure (760 mmHg).

Further, when the at least one hydroxyl group is chosen from terminal hydroxyl groups, the at least one hydroxyl group is in the α,ω position with respect to the —COOH functional group of the at least one aliphatic hydroxycarboxylic acid.

The at least one ester may be chosen from those esters which exhibit a viscosity of greater than 500 cP (50 Pa.s) at 20° C. as well as at 23° C., such as from 900 cP to 10,000 cP (95 Pa.s to 1000 Pa.s), and further such as from 950 cP to 5000 cP (95 Pa.s to 500 Pa.s), measured with a viscometer of the Brookfield RV type or a viscometer of the Brookfield "DV-II+" type of LV type equipped with a No. 1 rotor rotating from 0.5 tr/min to 10 tr/min, after 10 minutes, and/or a refractive index of at least 1.48, such as ranging from 1.48 to 1.55 (the refractive index being defined for the D line of sodium).

The at least one aromatic acid can be chosen from carboxylic acids chosen from:
(a) monoacids, such as benzoic acid, phenylacetic acid, cinnamic acid, 3-phenylpropanoic acid and salicyclic acid;
(b) diacids, such as terephthalic acid;
(c) triacids, such as trimellitic acid; and
(d) tetraacids, such as pyromellitic acid.

In one embodiment, the at least one aromatic acid is chosen from benzoic acid.

The at least one ester which can be used according to the present invention may be derived from esterification by (i) at least one aromatic acid of (ii) at least one hydroxylated aliphatic carboxylic acid. Non-limiting examples of the at least one hydroxylated aliphatic carboxylic acid include:

(i) saturated linear monohydroxylated aliphatic monoacids chosen from: monoacids of formula (1):

(1)

wherein $0 \leq x+y \leq 37$.

Non-limiting examples of monoacids (1) include lactic acid (x+y=0), 12-hydroxyoctadecanoic acid (also called 12-hydroxystearic acid) of formula:

that is, those wherein x=5, y=10 and x+y=15; and α-hydroxyoctadecanoic acid of formula:

that is, those wherein x=5 and y=0; and monoacids of formula (2):

(2)

wherein $0 \leq x \leq 38$.

Non-limiting examples of monoacids of formula (2) include glycolic acid (HO—$CH_2$—COOH), that is, those wherein x=0, and juniperic acid (16-hydroxyhexadecanoic acid) of formula HO—$CH_2$—$(CH_2)_{14}$—COOH, that is, those wherein x=14;

(ii) saturated branched monohydroxylated aliphatic monoacids of formula (3):

(3)

wherein $0 \leq x+y \leq 35$.

Non-limiting examples of monoacids of formula (3) include 5-methyl-2-hydroxyhexanoic acid (leucinic acid) of formula:

that is, those wherein x=1, y=0 and x+y=1, and 2-ethyl-3-hydrocaprylic acid of formula:

(iii) unsaturated monohydroxylated aliphatic monoacids of formula (4):

wherein $0 \leq x+y+z \leq 35$.

Non-limiting examples of monoacids of formula (4) include cis-12-hydroxy-9-octadecanoic acid (also called ricinoleic acid) of formula:

that is, those wherein x=5, y=1, z=7 and x+y+z=13; and monoacids of formula (5):

wherein $0 \leq x+y+z \leq 35$.

Non-limiting examples of monoacids of formula (5) include 3-hydroxy-4-hexanoic acid of formula:

that is, those wherein x=0, y=0 and z=1 and x+y+z=1; and 2-hydroxy-15-tetracosenoic acid (also called oxynervonic acid) of formula:

that is, those wherein x=7, y=12 and z=0 and x+y+z=17; and monoacids of formula (6):

wherein $0 \leq x+y \leq 36$.

Non-limiting examples of monoacids of formula (6) include 16-hydroxy-6-hexadecenoic acid of formula HO—CH$_2$—(CH$_2$)$_8$—CH═CH—(CH$_2$)$_4$—COOH, that is, those wherein x=8, y=4 and x+y=12;

(iv) saturated polyhydroxylated aliphatic monoacids of formula (7):

wherein $0 \leq x+y+z \leq 36$.

Non-limiting examples of monoacids of formula (7) include 9,10-dihydroxyoctadecanoic acid of formula:

that is, those wherein x=7, y=0, z=7 and x+y+z=14, 9,12-dihydroxyoctadecanoic acid wherein x=5, y=2, z=7 and x+y+z=14, 9,10,16-trihydroxyhexadecanoic acid (aleuritic acid), 9,10,12-trihydroxyoctadecanoic acid of formula:

hexahydroxyoctadecanoic acid and octahydroxyoctadecanoic acid;

(v) saturated monohydroxylated aliphatic polyacids of formula (8):

wherein $0 \leq x+y \leq 37$.

Non-limiting examples of polyacids of formula (8) include malic acid and citric acid; and (vi) saturated polyhydroxylated aliphatic polyacids. Non-limiting examples of saturated polyhydroxylated aliphatic polyacids include tartaric acid.

In one embodiment, the at least one hydroxylated aliphatic compound can be chosen from those resulting from esterification by at least one aromatic acid of at least one ester of at least one hydroxylated aliphatic acid, wherein said at least one ester of at least one hydroxylated aliphatic acid is chosen from:

(vii) esters of saturated linear monohydroxylated aliphatic monoacids. Non-limiting examples of such esters include esters of lactic acid (such as isosteraryl lactate, lactate resulting from $C_{12}$–$C_{13}$ alcohol, octyldodecyl lactate, oleyl lactate and myristyl lactate) and esters of 12-hydroxyoctadecanoic acid (also called 12-hydroxystearic acid) (such as 2-ethylhexyl hydroxystearate, octyldodecyl hydroxystearate, isostearyl hydroxystearate, isodecyl hydroxystearate, glyceryl trihydroxystearate (also called hydrogenated castor oil) and dipentaerythrityl hexahydroxystearate);

(viii) esters of unsaturated monohydroxylated aliphatic monoacids. Non-limiting examples of such esters include esters of ricinoleic acid (also called cis-12-hydroxy-9-octadecanoic acid) (such as butyl ricinoleate, octyldodecyl ricinoleate, cetyl ricinoleate and glyceryl triricinoleate (also called castor oil));

(ix) esters of saturated monohydroxylated aliphatic polyacids. Non-limiting examples of such esters include diisostearyl malate, triisostearyl citrate and trioctyl dodecyl citrate); and (x) esters of saturated polyhydroxylated aliphatic polyacids. Non-limiting examples of such esters include tartrates derived from reaction with two branched $C_{12}$–$C_{13}$ alcohols.

According to the present invention, the at least one hydroxylated aliphatic compound can be derived from esterification of at least one polyol with at least one ester of at least one hydroxylated aliphatic acid, wherein said at least one hydroxylated aliphatic compound can be chosen from:

(xi) partial and complete esters derived from esterification of at least one hydroxylated aliphatic acid by at least one $C_2$ to $C_{16}$ polyol (such as triglycerides, pentaerythritol, neopentyl glycol, dipentaerythritol esters, polyglycerol esters and sorbitol esters).

In one embodiment, the at least one ester is chosen from aliphatic fatty acid esters comprising at least one ester of an ester, wherein the ester groups may be identical or different and wherein the fatty acid residue comprises at least 12 carbon atoms. In another to embodiment, the at least one hydroxylated aliphatic compound is chosen from esters of ricinoleic acid, esters of 12-hydrostearic acid, esters of lactic acid and esters of 14-hydroxyeicosenoic acid.

For example, the at least one ester may be chosen from:

esters derived from esterification of castor oil with benzoic acid in a proportion of 1 to 1 (1/1), such as that sold by Finetex as Finsolv BCO-110, which will subsequently be referred to as "glyceryl monobenzoyl ricinoleate";

esters derived from esterification of castor oil with benzoic acid in a proportion of 1 to 1.5 (1/1.5), such as that sold by Finetex as Finsolv BCO-115, which will subsequently be referred to as "glyceryl mono/dibenzoyl ricinoleate";

esters derived from esterification of castor oil with benzoic acid in a proportion of 1 to 2 (1/2), such as that sold by Finetex as Finsolv BCO-120, which will subsequently be referred to as "glyceryl dibenzoyl ricinoleate"; and esters derived from esterification of castor oil with benzoic acid in a proportion of 1 to 3 (1/3), such as that sold by Finetex as Finsolv BCO-130, which will subsequently be referred to as "glyceryl tribenzoyl ricinoleate."

Ricinoleic acid constitutes from 80% to 92% of castor oil. The esterification of castor oil, therefore, results predominantly (80% to 92%) in at least one ester of an ester of ricinoleic acid.

According to the present invention, the at least one ester may be chosen from esters derived from esterification with benzoic acid of lesquerella oil (which comprises from 52% to 57% of an ester of 14-hydroxyeicosenoic acid (also called lesquerolic acid)).

The at least one ester chosen from aromatic esters of castor oil are known to have higher viscosities and refractive indices than those of castor oil:

|  | Castor oil | Finsolv BCO110 | Finsolv BCO115 | Finsolv BCO120 | Finsolv BCO130 |
|---|---|---|---|---|---|
| Viscosity at 20° C. (cP)** | 786 (78.6 Pa · s) (4)* | 1008 (100.8 Pa · s) (4)* | 2699 (269.9 Pa · s) (1)* | 1045 (104.5 Pa · s) (4)* | 918 (91.8 Pa · s) (4)* |
| Viscosity at 23° C. (cP)*** | 844 (84.4 Pa · s) (10)* | 971 (97.1 Pa · s) (10)* | — | 1036 (103.6 Pa · s) (5)* | 1090 (109 Pa · s) (5)* |
| Refractive index at 25° C. | 1.475 | 1.488 | 1.494 | 1.496 | 1.498 |

(*rotational speed in rev/min).
(**the viscosity at 20° C. was measured with a Brookfield "DV-II+" type LV viscometer with a No. 1 rotor).
(***the viscosity at 23° C. was measured with a Brookfield RV viscometer equipped with a No. 1 rotor).

The esters (other than castor oil) in the above table each have higher viscosities and refractive indices than those of castor oil.

Further, the at least one ester in accordance with the present invention may also exhibit better dispersing properties with respect to their ability to homogeneously disperse solid particles, such as, for example, pigments and fillers, than castor oil. For example, brown iron oxide was better dispersed when the cosmetic composition comprised at least one ester in accordance with the present invention than it was when castor oil was used. See Examples.

According to the present invention, the at least one ester may absorb less water than does castor oil. For example, Fisolv BCO-115, Finsolv BCO-120 and Finsolv 130 absorbed less water than did castor oil See Examples. Thus, the at least one ester may have a reduced tendency to cause problems of stability, for example in areas where there is a high degree of humidity.

Finally, at least one of the cosmetic properties, such as the stickiness, of the at least one ester in accordance with the present invention is comparable to that of castor oil and is superior to those of polybutene (Indopol H 1500) for a comparable gloss. See Examples.

The at least one ester of the inventive composition may be synthesized according to the process disclosed in U.S. Pat. No. 5,959,130, the disclosure of which is incorporated herein by reference.

According to the present invention, the at least one ester can be present in an amount generally ranging from 0.1% to 99.9% by weight relative to the total weight of the compositions, such as from 1% to 99%, and further such as from 5% to 90%, and can generally be present in an amount sufficient to confer to the inventive composition at least one property chosen from nongreasiness, non-stickiness, slip, gloss, coverage stability and hold over time.

The present invention is directed to cosmetic and dermatological products which may be or may not be colored. In one embodiment, the present invention is directed to lipstick products.

The inventive compositions can be provided in the form of a solid composition, compacted or cast as a stick, compacted or cast as a dish, and can be provided as pasty compositions and liquid compositions. In one embodiment, the inventive compositions are provided in the form of a solid, that is, in a hard form (not flowing under its own weight), such as in a cast or compacted form, for example as a stick or a dish.

As mentioned, the composition can be provided in the form of a paste, a solid or a cream. For example, the composition can be an oil-in-water emulsion, a water-in-oil emulsion, a solid anhydrous gel, a soft anhydrous gel, a free powder, a compacted powder and a two-phase form. For example, the composition can be provided in the form of a composition with at least one oily continuous phase, such as at least one anhydrous oily continuous phase, wherein the at least one continuous phase may comprise at least one aqueous phase in an amount ranging up to 10% by weight relative to the total weight of the composition, such as up to 5% by weight.

The inventive compositions may further comprise at least one coloring material. The at least one coloring material may be chosen from dyes which are soluble in the composition, dyes which are dispersible in the composition, pigments and pearlescent agents. Non-limiting examples of dyes include fat-soluble dyes and water-soluble dyes. The at least one coloring material, if present, may be present in an amount generally ranging from 0.001% to 98% by weight relative to the total weight of the composition, such as from 0.5% to 85%, and further such as from 1% to 60%.

For example, when the at least one coloring material is present in an amount greater than 50% by weight relative to the total weight of the inventive composition, it is generally intended for a composition in powder form, in which case, the at least one ester can constitute all or part of the powder binder.

Further, for a composition in the form of a paste or in cast form, such as foundation products, lipstick products and products for making up the body, the at least one coloring material is generally present in an amount ranging from 0.5% to 50% by weight relative to the total weight of the composition, such as from 2% to 40%, and further such as from 5% to 30%.

Non-limiting examples of fat-soluble dyes are Soudan red, D & C Red 17, D & C Green 6, β-carotene, soybean oil, Soudan brown, D & C Yellow 11, D & C Violet 2, D & C Orange 5, and quinoline yellow. The at least one coloring material, when chosen from fat-soluble dyes, may be present in an amount generally ranging up to 20% by weight relative to the total weight of the composition, such as, if present, from 0.1% to 6%.

Non-limiting examples of water-soluble dyes are beet juice and methylene blue. The at least one coloring material, if present and chosen from water-soluble dyes, may be present in an amount generally ranging from 0.1% to 6% by weight relative to the total weight of the composition.

The inventive compositions may further comprise at least one particulate filler. The at least one particulate filler, if present, may be present in an amount generally ranging up to 50% by weight relative to the total weight of the composition, such as from 0.01% to 40%, and further such as from 0.05% to 30%. The at least one particulate filler may be chosen from pigments commonly used in cosmetic or dermatological compositions, pearlescent agents commonly used in cosmetic or dermatological compositions and fillers commonly used in cosmetic or dermatological compositions.

As used herein, "pigments" refers to white and colored, organic and inorganic particles which are insoluble in the at least one liquid fatty phase and which are intended to color and/or opacity the composition. As used herein, "fillers" refer to colorless and white, inorganic and synthetic, lamellar and non-lamellar particles. As used herein, "pearlescent agents" refer to iridescent particles produced by certain molluscs in their shells and those which may be synthesized. The fillers and pearlescent agents may be used to modify the texture of the composition.

According to the present invention, the pigments, if present, can be present in an amount generally ranging from 0.05% to 30% by weight relative to the total weight of the composition, such as from 2% to 20%. Non-limiting examples of inorganic pigments include titanium oxides, zirconium oxides, cerium oxides, zinc oxides, iron oxides, chromium oxides and ferric blue. Non-limiting examples of organic pigments include carbon black and barium lakes, strontium lakes, calcium lakes (such as D & C Red No. 7) and aluminum lakes.

The pearlescent agents, if present, can be present in an amount generally ranging up to 20% by weight relative to the total weight of the composition, such as from 1% to 15%. Non-limiting examples of pearlescent agents include mica covered with titanium oxide, mica covered with iron oxide, mica covered with natural pigment, mica covered with bismuth oxychloride, and goniochromatic pigments. In one embodiment, the pearlescent agents are chosen from colored titanium oxide-coated mica and interferential multilayer pigments.

The fillers, if present, can be present in an amount generally ranging up to 35% by weight of the total weight of the composition, such as from 0.5% to 15%. Non-limiting examples of fillers include talc, mica, kaolin, powders formed of Nylon® (such as Orgasol), powders formed of polyethylene, powders formed of polytetrafluoroethylene (Teflon®), starch, boron nitride, microspheres formed of copolymers and silicone resin microbeads. Non-limiting examples of microspheres formed of copolymers include Expancel® (Nobel Industry), Polytrap® (Dow Corning) and Polypore® L 200 (Chemdal Corporation). A non-limiting example of silicone resin microbeads is Tospearl® (Toshiba).

According to the present invention, the compositions may further comprise at least one additional fatty substance, different from said at least one ester. The at least one additional fatty substance may be chosen from waxes, fatty substances (also referred to as "oils") which are liquid at room temperature (25° C.) and atmospheric pressure (760 mmHg) different from said at least one ester, fatty substances which are pasty at room temperature, gums, resins and lipophilic polymers.

The inventive compositions may also further comprise at least one wax. As used herein, "wax" refers to a lipophilic fatty compound which: (1) is solid at room temperature (25° C.) with a reversible solid/liquid change of state, (2) has a melting temperature of greater than 30° C. (which can be up to 200° C.) and (3) has an anisotropic crystal organization in the solid state. The size of the crystals is such that the crystals diffract and/or scatter light, thereby giving the composition a relatively opaque, cloudy appearance. It may be possible to make the wax miscible with oils by bringing the wax to its melting point, and, thereby, to form a microscopically homogeneous mixture but once the mixture has returned to room temperature, recrystallization of the wax occurs in the oils of the composition.

The at least one wax can be chosen from compounds which are solid at room temperature and which are intended to structure the composition, for example, in the form of a stick. For example, the at least one wax can be chosen from hydrocarboneous waxes, fluorinated waxes, and silicone waxes and can be chosen from waxes of vegetable origin, mineral origin, animal origin and synthetic origin. In one embodiment, the at least one wax has a melting temperature of greater than 30° C., such as greater than 45° C.

The at least one wax can be chosen from those conventionally used in cosmetic products and dermatological products. Non-limiting examples of the at least one wax include waxes of natural origin, optionally modified, (such as lanolin wax, oxypropylenated lanolin wax, acetylated lanolin wax, beeswax, carnauba wax, candelilla wax, ouricury wax, Japan wax, cork fiber wax, sugar cane wax, rice wax, montan wax, paraffin wax, lignite wax, microcrystalline wax, ceresin and ozokerites and hydrogenated oils (such as hydrogenated jojoba oil and hydrogenated castor oil)) and waxes of synthetic origin (such as polyethylene waxes derived from polymerization of ethylene, polyethylene waxes derived from copolymerization of ethylene, waxes obtained by Fischer-Tropsch synthesis, fatty acid esters different from the at least one ester (such as octacosanyl stearate, and glycerides that are solid at 30° C., such as at 45° C.), and silicone waxes (such as alkyl dimethicones and alkyl dimethicones, wherein the alkyl or alkoxy group comprises from 10 to 45 carbon atoms and poly(di)methylsiloxane esters which are solid at 30° C., wherein the ester chain comprises at least 10 carbon atoms)).

Due to the good dispersion of the particulate phase in the inventive compositions, the at least one wax may be crystallized. Such crystallization may result in an integrity and a homogeneity of the crystal lattice of the at least one wax which may reinforce at least one of the mechanical properties of the composition. For example, the hardness of a product in the form of a stick may be increased in compositions comprising the at least one ester relative to a composition of the prior art which does not comprise at least ester according to the present invention.

The hardness may be measured by a "butter-cutting" method, which involves cutting a 12.7 mm tube of a lip composition and measuring its hardness at 20° C. using a DFGHS 2 dynanometer from Indelco-Chatillon Co. at a speed of 100 mm/minute. The hardness value from this method is expressed in grams as the shear force required to cut a stick under the above conditions. According to this method, the hardness of compositions according to the present invention which may be in stick form may generally range from 50 g to 300 g, such as from 100 g to 250 g, and further such as from 150 g to 230 g.

According to the present invention, the gums which can be used are generally dissolved in an oil, the polymers are solid at room temperature and the resins can be liquid or solid at room temperature.

Both the nature and the amount of each of the gums, pasty substances and at least one wax depend on the desired mechanical properties and texture of the inventive composition. For example, the composition can comprise at least one wax in an amount generally ranging from 0.01% to 50% by weight relative to the total weight of the composition, such as from 25 to 40%, and further such as from 5% to 30%.

The oils, if present, can be chosen from hydrocarboneous oils, fluorinated oils, and silicone oils and can be chosen from oils of vegetable origin, mineral origin, animal origin and synthetic origin. As used herein, "hydrocarbonaceous oil" refers to an oil comprising carbon atoms and hydrogen atoms, optionally comprising at least one functional group chosen from hydroxyl groups, ester groups, ether groups and carboxyl groups.

Non-limiting examples of oils which can be used in the present invention include:

hydrocarbonaceous oils of animal origin, such as perhydrosqualene;

hydrocarbonaceous vegetable oils, such as liquid triglycerides of fatty acids comprising from 4 to 24 carbon atoms (such as triglycerides, heptanoic acid and octanoic acid), sunflower oil, maize oil, soybean oil, gourd oil, grape seed oil, sesame oil, hazelnut oil, apricot oil, macadamia oil, castor oil, avocado oil, triglycerides of caprylic/capric acids (such as those sold by Stéarineries Dubois and those sold as Miglyol 810, Miglyol 812 and Miglyol 818 by Dynamit Nobel), jojoba oil and karite butter;

linear and branched hydrocarbons of mineral and synthetic origin, such as liquid parrafins, derivatives of liquid parrafins, liquid petroleum, polydecenes and hydrogenated polyisobutene, such as parleam;

synthetic esters and synthetic ethers, such as synthetic esters of fatty acid and synthetic ethers of fatty acids, for example oils of formula $R_1COOR_2$ wherein $R_1$ is chosen from residues of higher fatty acid groups comprising from 1 to 40 carbon atoms and $R_2$ is chosen from hydrocarbonaceous groups comprising from 1 to 40 carbon atoms, with the proviso that the total number of carbon atoms in $R_1$ and $R_2$ is greater than or equal to 10 (such as, for example, purcellin oil, isononyl isononanoate, isopropyl myristate, 2-ethylhexyl palmitate, 2-octyldodecyl stearate, 2-octyldodecyl erucate, isostearyl isostearate), hydroxylated esters (such as isostearyl lactare, octyl hydroxystearate, octyldodecyl hydroxystearate, diisostearyl malate, triisocetyl citrate, fatty alcohol heptanoates, fatty alcohol octanoates, fatty alcoholdecanoates, polyol esters (such as propylene glycol dioctanoate, neopentyl glycol diheptanoate, diethylene glycol diisononanoate and pentaerythritol esters (such as pentaerythrityl tetraisostearate);

fatty alcohols comprising from 12 to 26 carbon atoms (such as octyldodecanol, 2-butyloctanol, 2-hexyldecanol, 2-undecylpentadecanol and oleyl alcohol)

fluorinated oils optionally partially hydrocarbonaceous and optionally partially silicone-comprising;

silicone oils, such as volatile and nonvolatile, linear, branched and cyclic polydimethylsiloxanes (PDMSs), polydimethylsiloxanes comprising groups chosen from alkyl groups, alkoxy groups and phenyl groups, optionally pendant or terminal, and each comprising from 2 to 24 carbon atoms, phenylsilicones (such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates); and mixtures of any of the foregoing.

The oils, if present, can be present in an amount generally ranging up to 90% by weight relative to the total weight of the composition, such as from 0.05% to 60% and further such as from 1% to 35%.

According to the present invention, the composition can further comprise at least one additive conventionally used in the fields of the present invention, and may be chosen from water, antioxidants, preservatives, neutralizing agents, lipophilic gelling agents, agent for gelling liquid fatty substances, agents for gelling the aqueous phase, dispersing agents, cosmetic active principles and dermatological active principles.

The at least one additive, with the exception of water, if present, can be present in an amount generally ranging up to 20% by weight relative to the total weight of the composition, such as up to 10%. When the at least one additive is chosen from water, the water, if present, can be present in an amount generally ranging up to 70% by weight relative to the total weight of the composition, such as from 1% to 50% and further such as from 1% to 10%.

When the inventive composition is in the form of an emulsion or dispersion of at least one aqueous phase in at least one fatty phase, the inventive composition can further comprise at least one emulsifying agent. The at least one ester, due to its ability to disperse solid particles (or at least one particulate phase), may facilitate the production of emulsions which are stable over time, that is, which do not show phase separation.

Needless to say, a person skilled in the art will take care to select the at least one suitable additive such that the advantageous properties of the composition in accordance with the invention are not, or are not substantially, adversely affected by the addition(s) envisaged.

According to the present invention, the compositions can be chosen from colored and non-colored dermatological compositions and colored and non-colored compositions for caring for at least one keratinous material (such as sun protection compositions and make-up removing compositions) and colored and non-colored hygienic compositions. Further, the inventive compositions may further comprise active principles chosen from cosmetic active principles and dermatological active principles. Therefore, for example, the compositions can be used as a base chosen from care bases and treatment bases for at least one keratinous material, such as the skin (for example the skin on hands and facial skin) and the lips (for example in the form of a lip balm product which may protect the lips from elements chosen from cold, sun and wind) and as a deodorant.

Non-limiting examples of cosmetic active principles which can be used in the invention include vitamin A, vitamin E, vitamin C, vitamin $B_3$, provitamins (such as D-panthenol), soothing active principles (such as α-bisabolol, aloe vera, allantoin, plant extracts and essential oils), protecting agents, restructuring agents (such as ceramides), freshness active principles (such as menthol and its derivatives), emollients (such as cocoa butter, dimethicone), moisturizing agents (such as arginine PCA), antiwrinkle active principles, essential fatty acids and mixtures of any of the foregoing.

The inventive compositions may be provided in the form of products for making up the skin, for example facial skin (such as foundation products and blusher products), paint products (such as semi-permanent tattooing products) and products for making up the lips (such as lipstick products and lip gloss products, wherein the inventive composition may optionally exhibit at least one property chosen from care properties and treatment properties) and products for making up the superficial body growths (such as nail varnish products, mascara products, eyeliner products, products for colouring hair and products for caring for hair).

Needless to say, the inventive compositions must be physiologically acceptable (cosmetically and/or dermatologically acceptable), namely nontoxic and capable of being applied to at least one keratinous material such as the skin, superficial body growths and lips of human beings.

According to the present invention, the compositions can be manufactured by known processes generally used in the cosmetic or dermatological field.

Another subject matter of the present invention is a mascara product, an eyeliner product, a foundation product, a lipstick product, a lipgloss product, a deodorant product, a make-up product for the body, a make-up-removing product, an eyeshadow product, a face powder product, a concealer product, a treating shampoo product, a hair conditioning product, an antisun product or a care product for the face or the body comprising at least one ester which is liquid at room temperature as defined above. For example, the at least one aromatic acid can be chosen from benzoic acid, phenylacetic acid, cinnamic acid, 3-phenylpropanoic acid and salicyclic acid, terephthalic acid, trimellitic acid and pyromellitic acid. In one embodiment, the at least one aromatic acid is benzoic acid.

Another subject matter of the present invention is a cosmetic process for caring for, making up or treating at least one keratinous material comprising applying to said at least one keratinous material a cosmetic composition as defined above. For example, the at least one aromatic acid can be chosen from benzoic acid, phenylacetic acid, cinnamic acid, 3-phenylpropanoic acid and salicyclic acid, terephthalic acid, trimellitic acid and pyromellitic acid. In one embodiment, the at least one aromatic acid is benzoic acid.

Yet another subject of the present invention is a process for making a composition film from a physiologically acceptable composition which has at least one property chosen from nonstickiness, nongreasiness, gloss, hold over time, good spreading and slip, comprising including in said composition at least one ester which is liquid at room temperature as defined above. For example, the at least one aromatic acid can be chosen from benzoic acid, phenylacetic acid, cinnamic acid, 3-phenylpropanoic acid and salicyclic acid, terephthalic acid, trimellitic acid and pyromellitic acid. In one embodiment, the at least one aromatic acid is benzoic acid.

The present invention is also directed to a process for dispersing at least one particulate filler in a composition comprising including in said composition at least one particulate filler and at least one ester which is liquid at room temperature as defined above. For example, the at least one aromatic acid can be chosen from benzoic acid, phenylacetic acid, cinnamic acid, 3-phenylpropanoic acid and salicyclic acid, terephthalic acid, trimellitic acid and pyromellitic acid. In one embodiment, the at least one aromatic acid is benzoic acid.

Another subject of the present invention is a process for limiting the exudation of a cast composition comprising including in said composition at least one ester which is liquid at room temperature as defined above. For example, the at least one aromatic acid can be chosen from benzoic acid, phenylacetic acid, cinnamic acid, 3-phenylpropanoic acid and salicyclic acid, terephthalic acid, trimellitic acid and pyromellitic acid. In one embodiment, the at least one aromatic acid is benzoic acid.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result. The percentages are given on a weight basis. In the continuation of the description, the hardnesses shown have all been measured according to the "butter-cutting wire" method indicated above.

EXAMPLES 1 to 3

Lipstick Stick Product

The inventors repeated Example No. 3 of the document of L'Oréal FR-A-2 745 580, the disclosure of which is incorporated herein by reference, for which they have successively substituted the polybutene sold under the reference Indopol H1500 by Amoco (recorded as Comparative Example 1) with:
  castor oil (Comparative Example 2), or
  glyceryl dibenzoyl ricinoleate (Finsolv BCO-120), (Example 3).

The compositions are given in Table (I).

TABLE I

|  | Ex. No. 1 (comparative) | Ex. No. 2 (comparative) | Ex. No. 3 (invention |
| --- | --- | --- | --- |
| Polybutene | 15.00 | — | — |
| Castor oil | — | 15.00 | — |
| Glyceryl dibenzoyl | — | — | 15.00 |
| Benzoate $C_{12}$–$C_{15}$ alkyls | 20.00 | 20.00 | 20.00 |
| Tridecyl tri-mellitate | 15.00 | 15.00 | 15.00 |
| Phenyl tri-methicone (DC556) | 5.00 | 5.00 | 5.00 |
| Diisostearyl malate | 7.00 | 7.00 | 7.00 |
| Lanolin | 13.00 | 13.00 | 13.00 |
| Preservative, antioxidants | 0.10 | 0.10 | 0.10 |
| Polyethylene wax (Mw = 500) | 4.00 | 4.00 | 4.00 |
| Candelilla wax | 7.00 | 7.00 | 7.00 |
| Carnauba wax | 3.90 | 3.90 | 3.90 |
| Pigments | 10.00 | 10.00 | 10.00 |
|  | 100.00% by mass | 100.00% by mass | 100.00% by mass |

Procedure

The pigments were milled in the oily phase with a triple roll mill. The other constituents were subsequently added and the mixture was heated at 100° C. until homogeneous and until the waxes had completely melted. The mixture was then cast in a suitable mould in order to obtain sticks, which were subsequently packaged.

Sensory Evaluation

Examples 1 to 3 were compared two by two on a panel of experts by application by half-lips.

Thus, the composition 3 according to the invention was judged to have greater slip, to be softer, to have greater coverage, to be less sticky, to be more pleasant to wear and to have better hold than composition 1 and to be softer, to give a more homogeneous make up, to have greater coverage, to be less sticky, to be more pleasant, to have greater gloss and to have better hold over time than the composition 2.

Furthermore, the composition 3 exhibited a stick hardness of 223 g, greater than that of the compositions 1 and 2 of 206 g and 200 g respectively, for the same amount of ingredients. It was thus stronger from a mechanical viewpoint. In addition, in order to obtain a stick hardness identical to that of a stick of the prior art, the amount of wax was reduced, which improved the gloss of the stick.

EXAMPLES 4 and 5

Dispersion of the Pigments

The inventors compared the dispersing properties of the aromatic esters of the composition of the invention with those of castor oil with respect to the brown iron oxide sold under the reference Cosmetic Grade Red Iron Oxide BC-7051 by Warner-Jenkinson.

Procedure

In a first step, a mixture composed of 16.67% of brown iron oxide and 83.33% by mass of oil (2 g of pigment per 10 g of oil) was prepared and heated at 70° C. while manually mixing, so as to wet the pigment.

This mixture was subsequently milled with a triple roll mill with three passes being carried out. This milled material was then diluted by adding oil (88 g of oil for a mixture of 2 g of pigment and 10 g of oil at the start), so as to obtain a pigment dispersion comprising:

$$2.00\% \text{ of brown iron oxide} + \frac{98.00\% \text{ of oil}}{100.00\% \text{ by mass}}$$

A support composed of an "ash-free" filter paper with a porosity of 25 mm and a diameter of 90 mm, sold by Prolabo, which was impregnated in a crystallizing dish with the test oil preheated to 70° C., was prepared separately.

After impregnating, the excess oil was removed, so as to obtain a support with a mass of between 1.02 g and 1.18 g.

0.05 g of the dispersion was subsequently deposited at the centre of the support and the action of impregnation and of diffusion of the pigments in the support is allowed to take place for a period of 24 hours at room temperature (25° C.).

The diameter of the pigmentary halo obtained was measured using a millimeter ruler. The results are given in Table (II) below.

TABLE II

| Oil | Diameter (mm) of the pigmentary halo |
| --- | --- |
| Glyceryl monobenzoyl ricinoleate (Finsolv BCO 110) | 41 |
| Glyceryl tribenzoyl ricinoleate (Finsolv BCO 130) | 36 |
| Glyceryl mono/dibenzoyl ricinoleate (Finsolv BCO 115) | 40 |
| Glyceryl dibenzoyl ricinoleate (Finsolv BCO 120) | 35 |
| Castor oil | 27 |

These results show that the esters of the invention have dispersing properties with respect to brown iron oxide which are superior to those of castor oil. The greater the diameter, the better the dispersion.

EXAMPLES 6 and 7

Absorption of Water

The inventors compared the water-absorbing properties of the aromatic esters of the composition of the invention with those of a composition comprising castor oil starting from a stick with the following formula:

| | |
|---|---|
| Octacosanyl stearate | 9.00% |
| Oil | 91.00% |
| | 100.00% by mass |

Procedure

The sticks were prepared in the usual way by heating the mixture at 100° C., so as to melt the wax, and then casting at this temperature in a suitable mould.

The sticks were subsequently stored in an oven at 25° C. and 90% relative humidity.

Figure 1:
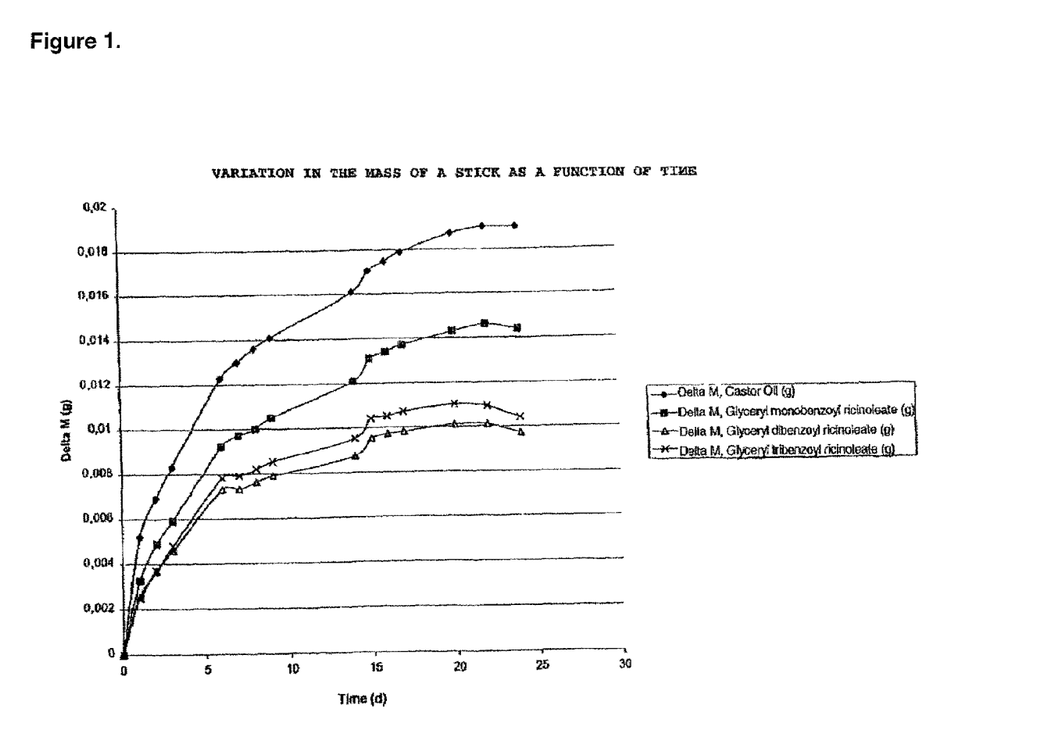
FIG. 1 is a graph showing the variation in the mass of each of four compositions in stick form as a function of time.

The increase in their mass over time was then measured, which increase corresponded to the absorption of water by the stick. The results are given on the appended graph, which gives the difference in mass Delta M (g) as a function of the time (d). This graph was drawn up from the data in Table (III).

TABLE III

| Time (days) | Delta M, Castor oil (g) | Delta M, Glyceryl monobenzoyl ricinoleate (g) | Delta M, Glyceryl dibenzoyl ricinoleate (g) | Delta M, Glyceryl tribenzoyl ricinoleate (g) |
|---|---|---|---|---|
| 0 | 0 | 0 | 0 | 0 |
| 1 | 0.0052 | 0.0033 | 0.0026 | 0.0025 |
| 2 | 0.0069 | 0.0049 | 0.0037 | 0.0037 |
| 3 | 0.0083 | 0.0059 | 0.0046 | 0.0048 |
| 6 | 0.0123 | 0.0092 | 0.0073 | 0.0078 |
| 7 | 0.013 | 0.0097 | 0.0073 | 0.0079 |
| 8 | 0.0136 | 0.01 | 0.0076 | 0.0082 |
| 9 | 0.0141 | 0.0105 | 0.0079 | 0.0085 |
| 14 | 0.0161 | 0.0121 | 0.0087 | 0.0095 |
| 15 | 0.0171 | 0.0131 | 0.0095 | 0.0104 |
| 16 | 0.0175 | 0.0134 | 0.0097 | 0.0105 |
| 17 | 0.0179 | 0.0137 | 0.0098 | 0.0107 |
| 20 | 0.0187 | 0.0143 | 0.0101 | 0.011 |
| 22 | 0.019 | 0.0146 | 0.0101 | 0.0109 |
| 24 | 0.019 | 0.0144 | 0.0097 | 0.0104 |

From this graph, it was observed that the sticks of the invention absorb less water than those comprising castor oil.

EXAMPLES 8 to 10

Lipstick

The examples of compositions are given in Table (IV) below.

TABLE IV

| | Example 8 (Comparative) | Example 9 (Comparative) | Example 10 (Invention |
|---|---|---|---|
| Polybutene | 15.58 | — | — |
| Castor oil | — | 15.58 | — |
| Glyceryl dibenzoyl ricinoleate (Finsolv BCO-120) | — | — | 15.58 |
| Benzoate of $C_{12}$–$C_{15}$ alkyls | 20.78 | 20.78 | 20.78 |
| Tridecyl tri-mellitate | 15.58 | 15.58 | 15.58 |
| Phenyltrimethicone (DC556) | 5.19 | 5.19 | 5.19 |
| Diisostearyl malate | 7.27 | 7.27 | 7.27 |
| Lanolin | 13.50 | 13.50 | 13.50 |
| Preservative, antioxidants | 0.10 | 0.10 | 0.10 |
| Polyethylene wax (MW = 500) | 3.22 | 3.22 | 3.22 |
| Candelilla wax | 5.64 | 5.64 | 5.64 |
| Carnauba wax | 3.14 | 3.14 | 3.14 |
| Pigments | 10.00 | 10.00 | 10.00 |
| | 100% by mass | 100% by mass | 100% by mass |

The sticks 8 to 10 were manufactured in accordance with Examples 1 to 3. The hardness of the sticks obtained for Examples 8, 9 and 10 was respectively 145 g, 137 g and 188 g. In these examples, a decrease in the level of wax with respect to Examples 1 to 3 was observed. With composition 10 of the invention, a hardness was obtained which is entirely acceptable for lipstick with less than 15% of wax. It exhibited improved gloss with respect to the compositions 8 and 9 according to the prior art.

Sensory Evaluation

These three compositions were compared two by two on a panel of seven experts by application as half lips. The readings with regard to the various criteria are between 0 (not) and 10 (very) inclusive. The results are given in Tables (V) and (VI) below.

1) Comparison of Examples Nos. 8 and 10

TABLE V

| Criteria evaluated | Ex. No. 8 (Comparative) Value Standard deviation | Ex. No. 10 (Invention) Value Standard deviation |
|---|---|---|
| On application of the stick to the lips | | |
| Slip | 3.6 ± 1.1 | 6.4 ± 0.8 |
| Softness | 5.0 ± 0.8 | 6.7 ± 2.0 |
| Stickiness | 4.1 ± 3.1 | 3.0 ± 1.4 |
| Homogeneity | 7.6 ± 0.8 | 7.6 ± 1.1 |
| Gloss | 7.0 ± 1.2 | 6.9 ± 1.2 |
| Coverage* | 7.0 ± 1.0 | 7.3 ± 1.0 |
| *After application | | |
| Stickiness | 4.9 ± 2.9 | 3.9 ± 2.2 |
| Gloss | 6.6 ± 1.0 | 6.7 ± 1.1 |
| Attractiveness of application | 5.0 ± 0.8 | 7.4 ± 1.0 |
| Quality of the product | 5.3 ± 0.8 | 7.1 ± 0.9 |
| *After application for 1 hour | | |
| Comfort | 6.1 ± 1.2 | 7.1 ± 1.6 |
| Stickiness | 3.9 ± 2.2 | 2.9 ± 2.1 |
| Hold | 5.7 ± 1.1 | 6.3 ± 0.8 |
| Gloss | 6.1 ± 1.4 | 5.7 ± 1.4 |
| General opinion | 4.9 ± 0.7 | 5.9 ± 1.4 |

(*The coverage is defined herein as the ability of a make-up composition to cover the substrate to which the said composition is applied, in particular for concealing the imperfections thereof).

The composition 10 of the invention had significantly greater slip on application than the composition 8; its attractiveness after application and the quality (cosmetic properties) of the product were also significantly superior to those of the composition 8.

The composition of the invention had a tendency to be less sticky and more comfortable than that of Example 8; the general opinion was that the inventive composition was superior to the composition of Example 8 in the aforementioned properties while retaining a comparable gloss.

2) Comparison of Examples Nos. 9 and 10

TABLE VI

| Criteria evaluted | Ex. No. 9 (Comparative) Value Standard deviation | Ex. No. 10 (Invention) Value Standard deviation |
|---|---|---|
| On application of the stick to the lips | | |
| Slip | 6.1 ± 1.1 | 6.0 ± 1.0 |
| Softness | 6.6 ± 1.3 | 7.0 ± 0.8 |
| Stickiness | 2.0 ± 1.4 | 2.1 ± 1.8 |
| Homogeneity | 6.4 ± 1.1 | 6.9 ± 1.1 |
| Gloss | 6.4 ± 1.0 | 6.4 ± 1.0 |
| Coverage | 6.6 ± 1.0 | 6.9 ± 0.7 |
| After application | | |
| Stickiness | 2.4 ± 1.5 | 3.0 ± 1.7 |
| Gloss | 6.6 ± 1.0 | 6.6 ± 1.0 |
| Attractiveness of application | 6.6 ± 1.0 | 7.1 ± 0.7 |
| Quality of the product | 6.3 ± 0.5 | 7.0 ± 0.8 |
| After application for 1 hour | | |
| Comfort | 6.0 ± 1.3 | 5.4 ± 1.3 |
| Stickiness | 3.1 ± 2.2 | 3.3 ± 2.2 |
| Hold | 6.3 ± 1.1 | 6.6 ± 1.0 |
| Gloss | 5.6 ± 1.1 | 5.9 ± 1.3 |
| General opinion | 5.4 ± 1.0 | 5.4 ± 1.4 |

The composition No. 10 according to the invention had a tendency to be of superior quality, after application, for a gloss which is comparable throughout the test to that of Example 9.

EXAMPLE 11

Lipstick Product

| | % by mass |
|---|---|
| Glyceryl mono/dibenzoyl ricinoleate (Finsolv BCO 115) | 15.58 |
| Benzoate of $C_{12}$–$C_{15}$ alkyls | 20.78 |
| Tridecyl trimellitate | 15.58 |
| Phenyltrimethicone (DC556) | 5.19 |
| Diisostearyl malate | 7.27 |
| Lanolin | 13.50 |
| Preservative, antioxidants | 0.10 |
| Polyethylene wax (Mw = 500) | 3.22 |
| Candelilla wax | 5.64 |
| Carnauba wax | 3.14 |
| Pigments | 10.00 |
| | 100% by mass |

This stick 11 was prepared in accordance with Examples 1 to 3. It exhibited a hardness of 160 g. The deposition of this makeup product on the lips was nongreasy, nonsticky, soft, glossy, covering, homogeneous, had good hold and was pleasant to wear throughout the day.

Absorption of Water

The stick of Example 10 and that of Example 11, packaged in a lipstick tube, were stored (without the cap and without the stick being outside the tube) in an oven at 30° C. and 70% relative humidity. The increase in mass over time was then measured. The results are given in Table (VII).

TABLE VII

| ABSORPTION OF WATER | | |
|---|---|---|
| Time (Days) | Delta Mass (g) Finsolv BCO-120 | Delta Mass (g) Finsolv BCO-115 |
| 0 | 0.0000 | 0.0000 |
| 1 | 0.0115 | 0.0109 |
| 2 | 0.0079 | 0.0054 |
| 5 | 0.0155 | 0.0178 |
| 6 | 0.0196 | 0.0169 |
| 7 | 0.0204 | 0.0187 |
| 8 | 0.0199 | 0.0173 |
| 9 | 0.0187 | 0.0193 |
| 12 | 0.0246 | 0.0224 |
| 13 | 0.0253 | 0.0226 |
| 14 | 0.0252 | 0.0220 |
| 15 | 0.0247 | 0.0233 |

It was found from this Table (VII) that the sticks according to the invention absorb little water. It was also found that the stick according to Example 11 absorbs even less water than that of Example 10.

EXAMPLES 12 and 13

Dispersion of Pigments

TABLE VIII

| | Oil, diameter (mm) of the pigmentary halo | |
|---|---|---|
| Pigment | Finsolv BCO 115 | Castor oil |
| Brown iron oxide | 40 | 27 |
| Red iron oxide | 40 | 26 |
| Yellow iron oxide | 39 | 24 |
| Black iron oxide | 23 | 22 |
| Titanium dioxide (sold by Kerr MacGee Chemical Corp. under the ref. Tronox CR837 CTFA) | 39 | 29 |
| FD & C Yellow No. 5 Al lake | 38 | 29 |
| FD & C Yellow No. 6 Al lake | 41 | 32 |
| D & C Red 7 | 37 | 29 |
| D & C Red 21 Al lake | 42 | 34 |
| D & C Red 27 Al lake | 38 | 30 |
| FD & C Blue No. 1 Al lake | 33 | 29 |

It was observed from Table (VIII) that, in all cases, the diameter of the halo, related to the quality of dispersion, was much greater with glyceryl mono/dibenzoyl ricinoleate (Finsolv BCO 115) with respect to castor oil.

What I claim is:

1. A lipgloss product comprising:
   (1) at least one particulate filler;
   (2) beeswax;
   (3) glyceryl dibenzoyl ricinoleate; and,
   (4) at least one coloring material.

2. The lipgloss product of claim 1, further comprising at least one fatty substance different from glyceryl dibenzoyl ricinoleate.

3. The lipgloss product of claim 2, wherein the at least one fatty substance different from glyceryl dibenzoyl ricinoleate comprises at least one oil.

4. The lipgloss product of claim 3, wherein the at least oil is chosen from jojoba oil, sunflower oil, and castor oil.

5. The lipgloss product of claim 1, wherein the at least one particulate filler is chosen from silica and mica.

6. The lipgloss product of claim 1, wherein the at least one coloring material is chosen from beet juice, titanium oxides, and iron oxides.

7. The lipgloss product of claim 1, wherein the lipgloss is in the form of a soft anhydrous gel.

8. The lipgloss product of claim 1, further comprising at least one additive chosen from water, antioxidants, preservatives, neutralizing agents, lipophilic gelling agents, agents for gelling liquid fatty substances, agents for gelling an aqueous phase, dispersing agents, cosmetic active principles, and dermatological active principles.

9. The lipgloss product of claim 8, wherein the at least one additive is a cosmetic active principle chosen from an essential oil.

10. A lipgloss product comprising:
(1) at least one particulate filler;
(2) at least one wax;
(3) glyceryl dibenzoyl ricinoleate; and,
(4) at least one coloring material.

11. The lipgloss product of claim 10, further comprising at least one fatty substance different from glyceryl dibenzoyl ricinoleate.

12. The lipgloss product of claim 11, wherein the at least one fatty substance different from glyceryl dibenzoyl ricinoleate comprises at least one oil.

13. The lipgloss product of claim 12, wherein the at least oil is chosen from jojoba oil, sunflower oil, and castor oil.

14. The lipgloss product of claim 10, wherein the at least one particulate filler is chosen from silica and mica.

15. The lipgloss product of claim 10, wherein the at least one coloring material is chosen from beet juice, titanium oxides, and iron oxides.

16. The lipgloss product of claim 10, wherein the at least one wax is beeswax.

17. The lipgloss product of claim 10, wherein the lipgloss is in the form of a soft anhydrous gel.

18. The lipgloss product of claim 10, further comprising at least one additive chosen from water, antioxidants, preservatives, neutralizing agents, lipophilic gelling agents, agents for gelling liquid fatty substances, agents for gelling an aqueous phase, dispersing agents, cosmetic active principles, and dermatological active principles.

19. The lipgloss product of claim 18, wherein the at least one additive is a cosmetic active principle chosen from an essential oil.

20. A lipgloss product comprising:
(1) at least one particulate filler;
(2) at least one wax;
(3) glyceryl mono/dibenzoyl ricinoleate; and,
(4) at least one coloring material.

21. The lipgloss product of claim 20, further comprising at least one fatty substance different from glyceryl mono/dibenzoyl ricinoleate.

22. The lipgloss product of claim 21, wherein the at least one fatty substance different from glyceryl mono/dibenzoyl ricinoleate comprises at least one oil.

23. The lipgloss product of claim 22, wherein the at least oil is chosen from jojoba oil, sunflower oil, and castor oil.

24. The lipgloss product of claim 20, wherein the at least one particulate filler is chosen from silica and mica.

25. The lipgloss product of claim 20, wherein the at least one coloring material is chosen from beet juice, titanium oxides, and iron oxides.

26. The lipgloss product of claim 20, wherein the at least one wax is beeswax.

27. The lipgloss product of claim 20, wherein the lipgloss is in the form of a soft anhydrous gel.

28. The lipgloss product of claim 20, further comprising at least one additive chosen from water, antioxidants, preservatives, neutralizing agents, lipophilic gelling agents, agents for gelling liquid fatty substances, agents for gelling an aqueous phase, dispersing agents, cosmetic active principles, and dermatological active principles.

29. The lipgloss product of claim 28, wherein the at least one additive is a cosmetic active principle chosen from an essential oil.

* * * * *